US012560560B2

(12) United States Patent
Schroeder et al.

(10) Patent No.: US 12,560,560 B2
(45) Date of Patent: Feb. 24, 2026

(54) AGRICULTURAL SYSTEM AND METHOD FOR MONITORING PLUGGING OF GROUND-ENGAGING TOOLS OF AN AGRICULTURAL IMPLEMENT

(71) Applicant: CNH Industrial America LLC, New Holland, PA (US)

(72) Inventors: Brittany Schroeder, Bunker Hill, IN (US); Joshua D. Knoblauch, Lowpoint, IL (US)

(73) Assignee: CNH Industrial America LLC, New Holland, PA (US)

( * ) Notice: Subject to any disclaimer, the term of this patent is extended or adjusted under 35 U.S.C. 154(b) by 389 days.

(21) Appl. No.: 18/448,327

(22) Filed: Aug. 11, 2023

(65) Prior Publication Data

US 2025/0052697 A1     Feb. 13, 2025

(51) Int. Cl.
    *G01N 22/04*     (2006.01)
    *A01B 29/04*     (2006.01)
    (Continued)

(52) U.S. Cl.
    CPC ........... *G01N 22/04* (2013.01); *A01B 29/048* (2013.01); *A01B 29/06* (2013.01); *G01N 33/24* (2013.01); *G01N 33/245* (2024.05)

(58) Field of Classification Search
    CPC ..... A01B 29/048; A01B 29/06; A01B 49/022; A01B 49/027; A01B 63/111;
    (Continued)

(56) References Cited

U.S. PATENT DOCUMENTS 3,863,428 A    2/1975   Baxter
4,286,424 A    9/1981   Hubbard
        (Continued)

FOREIGN PATENT DOCUMENTS

DE     102017112224 A1    12/2018
EP        1630574 B1      7/2013
        (Continued)

OTHER PUBLICATIONS

Conesa-Muñoz et al., Distributed Multi-Level Supervision to Effectively Monitor the Operations of a Fleet of Autonomous Vehicles in Agricultural Tasks, *Sensors* 2015, vol. 15, Issue 3, 2015, 5402-5428. https://doi.org/10.3390/s150305402.

*Primary Examiner* — Joseph M Rocca
*Assistant Examiner* — Robert E Pezzuto
(74) *Attorney, Agent, or Firm* — Dority & Manning, P.A.

(57) ABSTRACT

An agricultural system for monitoring plugging of a ground-engaging tool of an agricultural implement includes a signal transmission device configured to transmit wireless signals and a target provided in operative association with the ground-engaging tool, with the target being configured to receive the wireless signals transmitted from the signal transmission device. Additionally, the agricultural system includes a computing system configured to receive moisture data indicative of a moisture content within the field, adjust an output frequency for the signal transmission device to transmit the wireless signals from a current output frequency to an adjusted output frequency based at least in part on the moisture data, and determine when the ground-engaging tool is experiencing a plugged condition based at least in part on an attenuation parameter of the wireless signals transmitted by the signal transmission device at the adjusted output frequency and received by the target.

20 Claims, 5 Drawing Sheets

(51) Int. Cl.

| | | |
|---|---|---|
| *A01B 29/06* | (2006.01) | |
| *A01B 63/00* | (2006.01) | |
| *G01N 33/24* | (2006.01) | |

(58) Field of Classification Search

CPC ....... A01B 63/112; A01B 63/24; A01B 71/08; A01B 79/005; G01N 22/04; G01N 33/24

See application file for complete search history.

(56) References Cited

U.S. PATENT DOCUMENTS

| | | | |
|---|---|---|---|
| 5,063,729 | A | 11/1991 | Fox et al. |
| 5,425,223 | A | 6/1995 | Delaronde |
| 6,397,569 | B1 | 6/2002 | Homburg et al. |
| 6,438,506 | B1 | 8/2002 | Yohpe et al. |
| 6,956,348 | B2 | 10/2005 | Landry et al. |
| 6,990,390 | B2 | 1/2006 | Groth et al. |
| 7,143,836 | B2 | 12/2006 | Dietrich, Sr. |
| 7,354,341 | B1 | 4/2008 | Smith et al. |
| 8,326,500 | B2 | 12/2012 | Mariman et al. |
| 8,408,149 | B2 | 4/2013 | Rylander |
| 8,928,486 | B2 | 1/2015 | Hui et al. |
| 9,405,039 | B2 | 8/2016 | Anderson |
| 9,485,900 | B2 | 11/2016 | Connell et al. |
| 9,629,304 | B2 | 4/2017 | Zielke |
| 9,781,916 | B2 | 10/2017 | Preheim et al. |
| 10,076,072 | B2 | 9/2018 | Steinlage et al. |
| 10,151,839 | B2 | 12/2018 | Mcpeek |
| 10,194,573 | B2 | 2/2019 | Steinlage et al. |
| 10,255,670 | B1 | 4/2019 | Wu et al. |
| 10,765,052 | B2 | 9/2020 | DeGarmo |
| 11,058,045 | B2 | 7/2021 | Harmon |
| 11,191,202 | B2 | 12/2021 | Henry |
| 11,202,402 | B2 | 12/2021 | Glovier |
| 11,234,355 | B2 | 2/2022 | Smith et al. |
| 11,290,084 | B2 | 3/2022 | Nielsen et al. |
| 11,369,052 | B2 | 6/2022 | Cozza et al. |
| 2012/0291680 | A1 | 11/2012 | Rylander |
| 2013/0008361 | A1 | 1/2013 | Trevino et al. |
| 2014/0209337 | A1 | 7/2014 | Westland |
| 2015/0101519 | A1 | 4/2015 | Blackwell et al. |
| 2015/0257334 | A1 | 9/2015 | Wolters et al. |
| 2015/0296701 | A1 | 10/2015 | Anderson |
| 2015/0305224 | A1 | 10/2015 | Casper et al. |
| 2016/0088787 | A1 | 3/2016 | Connell et al. |
| 2017/0079192 | A1 | 3/2017 | Steinlage et al. |
| 2017/0086363 | A1 | 3/2017 | Tribelhorn |
| 2017/0359940 | A1 | 12/2017 | Bassett |
| 2018/0128933 | A1 | 5/2018 | Koch et al. |
| 2018/0139884 | A1 | 5/2018 | Karstens et al. |
| 2018/0206393 | A1 | 7/2018 | Stoller et al. |
| 2018/0279541 | A1 | 10/2018 | Kovach |
| 2018/0279542 | A1 | 10/2018 | Kovach |
| 2018/0279543 | A1 | 10/2018 | Kovach |
| 2018/0321386 | A1 | 11/2018 | Bosetti et al. |
| 2018/0352718 | A1 | 12/2018 | Kovach et al. |
| 2018/0364128 | A1 | 12/2018 | Stovall et al. |
| 2019/0174667 | A1 | 6/2019 | Gresch et al. |
| 2020/0037519 | A1 | 2/2020 | Wonderlich et al. |
| 2020/0100419 | A1 | 4/2020 | Stanhope |
| 2020/0107498 | A1 | 4/2020 | Anderson et al. |
| 2020/0128719 | A1 | 4/2020 | Harmon |
| 2020/0305335 | A1 | 10/2020 | Schoeny et al. |
| 2020/0355667 | A1 | 11/2020 | Schoeny |
| 2020/0387720 | A1 | 12/2020 | Stanhope |
| 2020/0404829 | A1 | 12/2020 | Knobloch et al. |
| 2020/0404830 | A1 | 12/2020 | Ferrari et al. |
| 2020/0404833 | A1 | 12/2020 | Stanhope et al. |
| 2021/0029865 | A1 | 2/2021 | Smith et al. |
| 2021/0105942 | A1 | 4/2021 | Paxinos et al. |
| 2024/0085347 | A1* | 3/2024 | Schroeder .............. A01B 47/00 |

FOREIGN PATENT DOCUMENTS

| | | | |
|---|---|---|---|
| EP | 3011815 | A1 | 4/2016 |
| EP | 3400763 | A1 | 11/2018 |
| JP | 2019/103431 | A | 6/2019 |
| WO | WO2018/020310 | A1 | 2/2018 |
| WO | WO2021/030519 | A1 | 2/2021 |

* cited by examiner

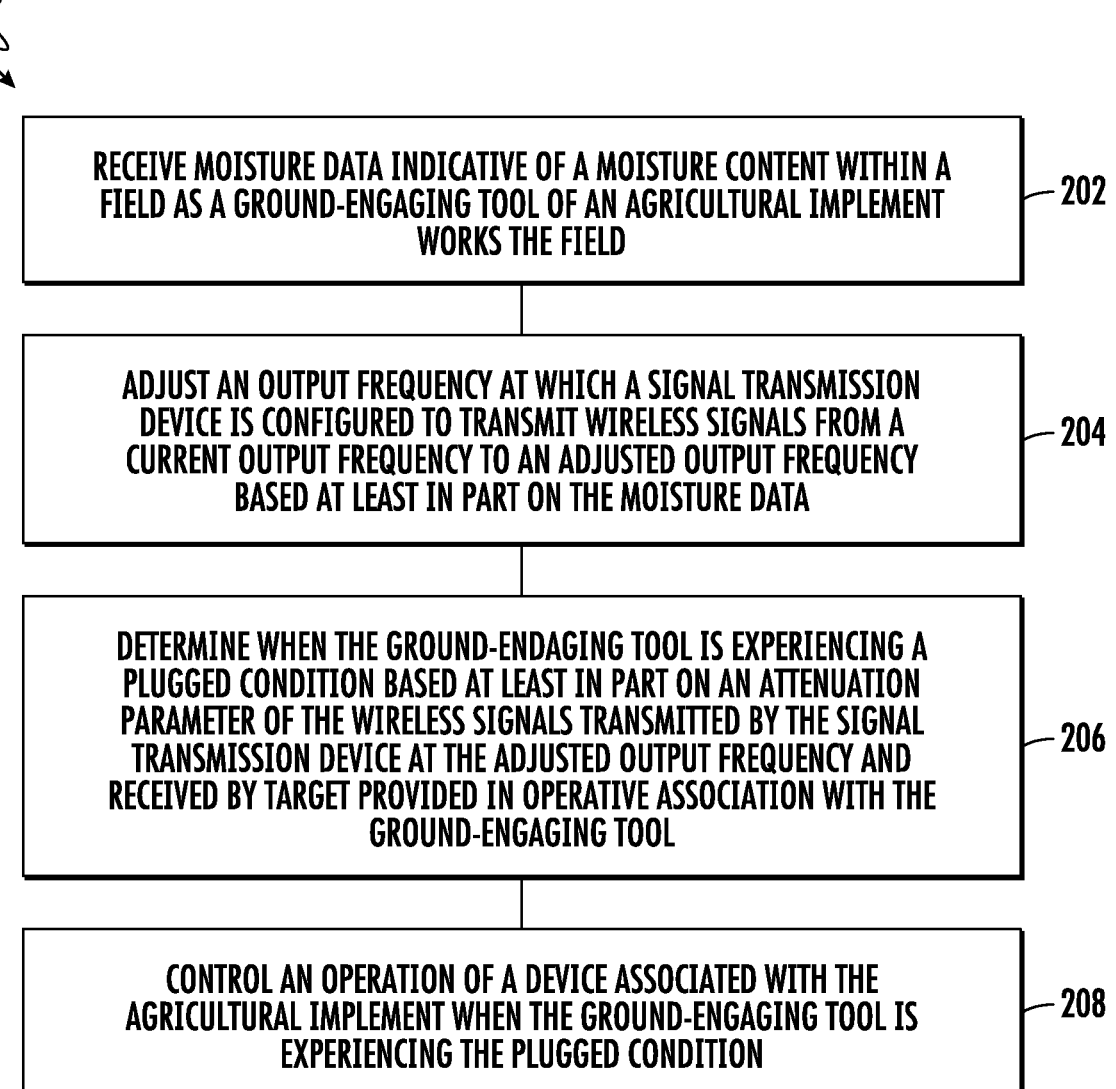

200

| RECEIVE MOISTURE DATA INDICATIVE OF A MOISTURE CONTENT WITHIN A FIELD AS A GROUND-ENGAGING TOOL OF AN AGRICULTURAL IMPLEMENT WORKS THE FIELD | 202 |

| ADJUST AN OUTPUT FREQUENCY AT WHICH A SIGNAL TRANSMISSION DEVICE IS CONFIGURED TO TRANSMIT WIRELESS SIGNALS FROM A CURRENT OUTPUT FREQUENCY TO AN ADJUSTED OUTPUT FREQUENCY BASED AT LEAST IN PART ON THE MOISTURE DATA | 204 |

| DETERMINE WHEN THE GROUND-ENDAGING TOOL IS EXPERIENCING A PLUGGED CONDITION BASED AT LEAST IN PART ON AN ATTENUATION PARAMETER OF THE WIRELESS SIGNALS TRANSMITTED BY THE SIGNAL TRANSMISSION DEVICE AT THE ADJUSTED OUTPUT FREQUENCY AND RECEIVED BY TARGET PROVIDED IN OPERATIVE ASSOCIATION WITH THE GROUND-ENGAGING TOOL | 206 |

| CONTROL AN OPERATION OF A DEVICE ASSOCIATED WITH THE AGRICULTURAL IMPLEMENT WHEN THE GROUND-ENGAGING TOOL IS EXPERIENCING THE PLUGGED CONDITION | 208 |

FIG. 5

AGRICULTURAL SYSTEM AND METHOD FOR MONITORING PLUGGING OF GROUND-ENGAGING TOOLS OF AN AGRICULTURAL IMPLEMENT

FIELD OF THE INVENTION

The present disclosure generally relates to agricultural implements and, more particularly, to systems and methods for identifying plugging of ground-engaging tools of an agricultural implement, such as rolling basket assemblies, based on wireless signal detection.

BACKGROUND OF THE INVENTION

It is well known that, to attain the best agricultural performance from a field, a farmer must cultivate the soil, typically through a tillage operation. Modern farmers perform tillage operations by pulling a tillage implement behind an agricultural work vehicle, such as a tractor. Tillage implements typically include one or more ground-engaging tools configured to engage the soil as the implement is moved across the field. For example, in certain configurations, the implement may include one or more harrow disks, leveling disks, rolling baskets, shanks, tines, and/or the like. Such ground-engaging tool(s) loosen and/or otherwise agitate the soil to prepare the field for subsequent planting operations.

During tillage operations, field materials, such as residue, soil, rocks, mud, and/or the like, may become trapped or otherwise accumulate on and/or within ground-engaging tools or between adjacent ground-engaging tools. For instance, material accumulation will often occur around the exterior of a basket assembly (e.g., on the blades or bars of the basket assembly) and/or within the interior of the basket assembly, within the curvature of shanks, between ganged disks, and/or the like. Such accumulation of field materials may prevent the basket assembly from performing in a desired manner during the performance of a tillage operation. In such instances, it is often necessary for the operator to take certain corrective actions to remove the material accumulation. However, it is typically difficult for the operator to detect or determine a plugged condition of a basket assembly or any other suitable ground-engaging tool(s) when viewing the tools from the operator's cab.

Accordingly, an improved system and method for monitoring plugging of ground-engaging tools of an agricultural implement would be welcomed in the technology.

BRIEF DESCRIPTION OF THE INVENTION

Aspects and advantages of the invention will be set forth in part in the following description, or may be obvious from the description, or may be learned through practice of the invention.

In one aspect, the present subject matter is directed to an agricultural system for monitoring plugging of ground-engaging tools of agricultural implements. More particularly, the agricultural system may include a ground-engaging tool of an agricultural implement, where the ground-engaging tool is configured to work a field as the agricultural implement is moved across the field. The agricultural system may further include a signal transmission device configured to transmit wireless signals, and a target provided in operative association with the ground-engaging tool and spaced apart from the signal transmission device. The target may generally be configured to receive the wireless signals transmitted from the signal transmission device. Additionally, the agricultural system may include a computing system configured to receive moisture data indicative of a moisture content within the field, adjust an output frequency for the signal transmission device to transmit the wireless signals from a current output frequency to an adjusted output frequency based at least in part on the moisture data, and determine when the ground-engaging tool is experiencing a plugged condition based at least in part on an attenuation parameter of the wireless signals transmitted by the signal transmission device at the adjusted output frequency and received by the target.

In another aspect, the present subject matter is directed to an agricultural method for monitoring plugging of ground-engaging tools of agricultural implements. More particularly, the agricultural method may include receiving, with a computing system, moisture data indicative of a moisture content within a field as a ground-engaging tool of an agricultural implement works the field as the agricultural implement is moved across the field. The agricultural method may further include adjusting, with the computing system, an output frequency at which a signal transmission device is configured to transmit wireless signals from a current output frequency to an adjusted output frequency based at least in part on the moisture data. Moreover, the agricultural method may include determining, with the computing system, when the ground-engaging tool is experiencing a plugged condition based at least in part on an attenuation parameter of the wireless signals transmitted by the signal transmission device at the adjusted output frequency and received by a target provided in operative association with the ground-engaging tool, where the target may be spaced apart from the signal transmission device. Additionally, the agricultural method may include controlling, with the computing system, an operation of a device associated with the agricultural implement when the ground-engaging tool is experiencing the plugged condition.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

3

Figure 1:
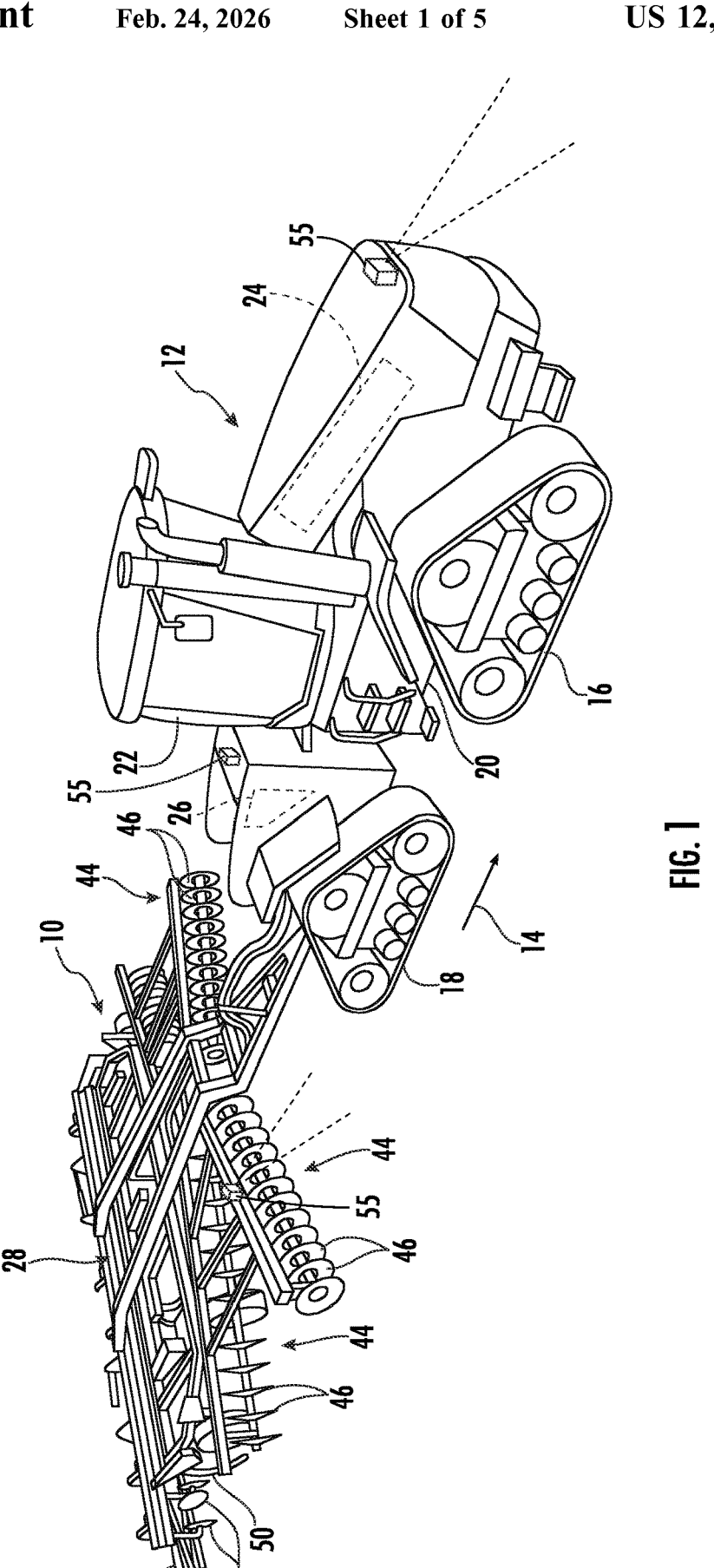
FIG. 1 illustrates a perspective view of one embodiment of an agricultural implement coupled to a work vehicle in accordance with aspects of the present subject matter.

FIG. 5 illustrates a flow diagram of one embodiment of a method for monitoring plugging of ground-engaging tools of an agricultural implement in accordance with aspects of the present subject matter.

Repeat use of reference characters in the present specification and drawings is intended to represent the same or analogous features or elements of the present technology.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a further embodiment. Thus, it is intended that the present invention covers such modifications and variations as come within the scope of the appended claims and their equivalents.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

As used herein, the terms "first," "second," and "third" may be used interchangeably to distinguish one component from another and are not intended to signify a location or importance of the individual components. The terms "coupled," "fixed," "attached to," and the like refer to both direct coupling, fixing, or attaching, as well as indirect coupling, fixing, or attaching through one or more intermediate components or features, unless otherwise specified herein. The terms "upstream" and "downstream" refer to the relative direction with respect to a harvested material within a fluid circuit. For example, "upstream" refers to the direction from which a harvested material flows, and "downstream" refers to the direction to which the harvested material moves. The term "selectively" refers to a component's ability to operate in various states (e.g., an ON state and an OFF state) based on manual and/or automatic control of the component.

Furthermore, any arrangement of components to achieve the same functionality is effectively "associated" such that the functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected" or "operably coupled" to each other to achieve the desired functionality, and any two components capable of being so associated can also be viewed as being "operably couplable" to each other to achieve the desired functionality. Some examples of operably couplable include, but are not limited to, physically mateable, physically interacting components, wirelessly interactable, wirelessly interacting components, logically interacting, and/or logically interactable components.

The singular forms "a," "an," and "the" include plural references unless the context clearly dictates otherwise.

Approximating language, as used herein throughout the specification and claims, is applied to modify any quantitative representation that could permissibly vary without resulting in a change in the basic function to which it is related. Accordingly, a value modified by a term or terms, such as "about," "approximately," "generally," and "substantially," is not to be limited to the precise value specified. In at least some instances, the approximating language may correspond to the precision of an instrument for measuring the value, or the precision of the methods or apparatus for constructing or manufacturing the components and/or systems. For example, the approximating language may refer to being within a ten percent margin.

Moreover, the technology of the present application will be described in relation to exemplary embodiments. The word "exemplary." is used herein to mean "serving as an example, instance, or illustration." Any embodiment described herein as "exemplary" is not necessarily to be construed as preferred or advantageous over other embodiments. Additionally, unless specifically identified otherwise, all embodiments described herein will be considered exemplary.

As used herein, the term "and/or," when used in a list of two or more items, means that any one of the listed items can be employed by itself, or any combination of two or more of the listed items can be employed. For example, if a composition or assembly is described as containing components A, B, and/or C, the composition or assembly can contain A alone; B alone; C alone; A and B in combination; A and C in combination; B and C in combination; or A, B, and C in combination.

In general, the present subject matter is directed to systems and methods for monitoring plugging of agricultural implements, particularly of ground-engaging tools of agricultural implements. Specifically, in several embodiments, the disclosed system may include one or more wireless signal transmission devices (e.g., an RFID reader) configured to wirelessly transmit signals to one or more associated targets (e.g., passive RFID tags), which may modify the wireless signals and return the modified wireless signals back to the wireless signal transmission devices (e.g., to the RFID reader). In general, the target(s) may be configured to be installed on, within, and/or adjacent to an associated ground-engaging tool at a suitable location that allows the transmission device(s) to transmit wireless signals to the targets(s) and receive modified wireless signals from the target(s), in response, during normal, non-plugged operation of the ground-engaging tool. However, with accumulation of field materials on, within, and/or adjacent to the ground-engaging tool, the wireless signals transmitted from the transmission device(s) to the target(s) (and thus, the modified signal(s) from the target(s) back to the transmission device(s)) will become degraded or attenuated (or may be completed blocked) as the signals pass through the accumulated material. By detecting the attenuation of the signals (or the lack of any signals due to signal blockage), an associated computing system of the disclosed system may infer or determine that the ground-engaging tool is currently plugged or experiencing a plugged condition. For instance, in one embodiment, the computing system may be configured to assess an attenuation parameter (e.g., signal strength) associated with the wireless signals received by the target (e.g., of the return signal from the target received at the wireless signal transmission device) to determine the existence of material accumulation on, within, and/or adjacent to the ground-engaging tool. Once it is determined that the ground-engaging tool is experiencing a plugged condition, an appropriate control action may then be executed, such as by notifying the operator of the plugged condition or by performing an automated control action.

However, the moisture content and/or the soil type within the field may affect the degree of attenuation of the wireless signals. For instance, the higher the moisture content within the field, the higher the degree of attenuation, which may cause the computing system to falsely detect plugging when plugging has not actually occurred, and/or to detect more significant plugging than is actually occurring, requiring more frequent inspections of the ground-engaging tools than necessary, and ultimately reducing productivity. Thus, in accordance with aspects of the present subject matter, the computing system may be configured to adjust an output frequency for the signal transmission device to transmit the wireless signals based at least in part on the moisture content within the field, then determining whether the ground-engaging tool is experiencing a plugged condition based at least in part on the attenuation of the signals transmitted at the adjusted output frequency. For instance, the output frequency (strength) for transmitting the wireless signals may be increased when the moisture content of the field is high, and the output frequency (strength) for transmitting the wireless signals may be decreased when the moisture content of the field is low. As such, the adjusted output frequency may be selected to account for changes in attenuation due to soil moisture to avoid false estimation of plugging severity when monitoring for a plugging condition of ground-engaging tools, which reduces inspection time, and increases productivity.

Figure 2:
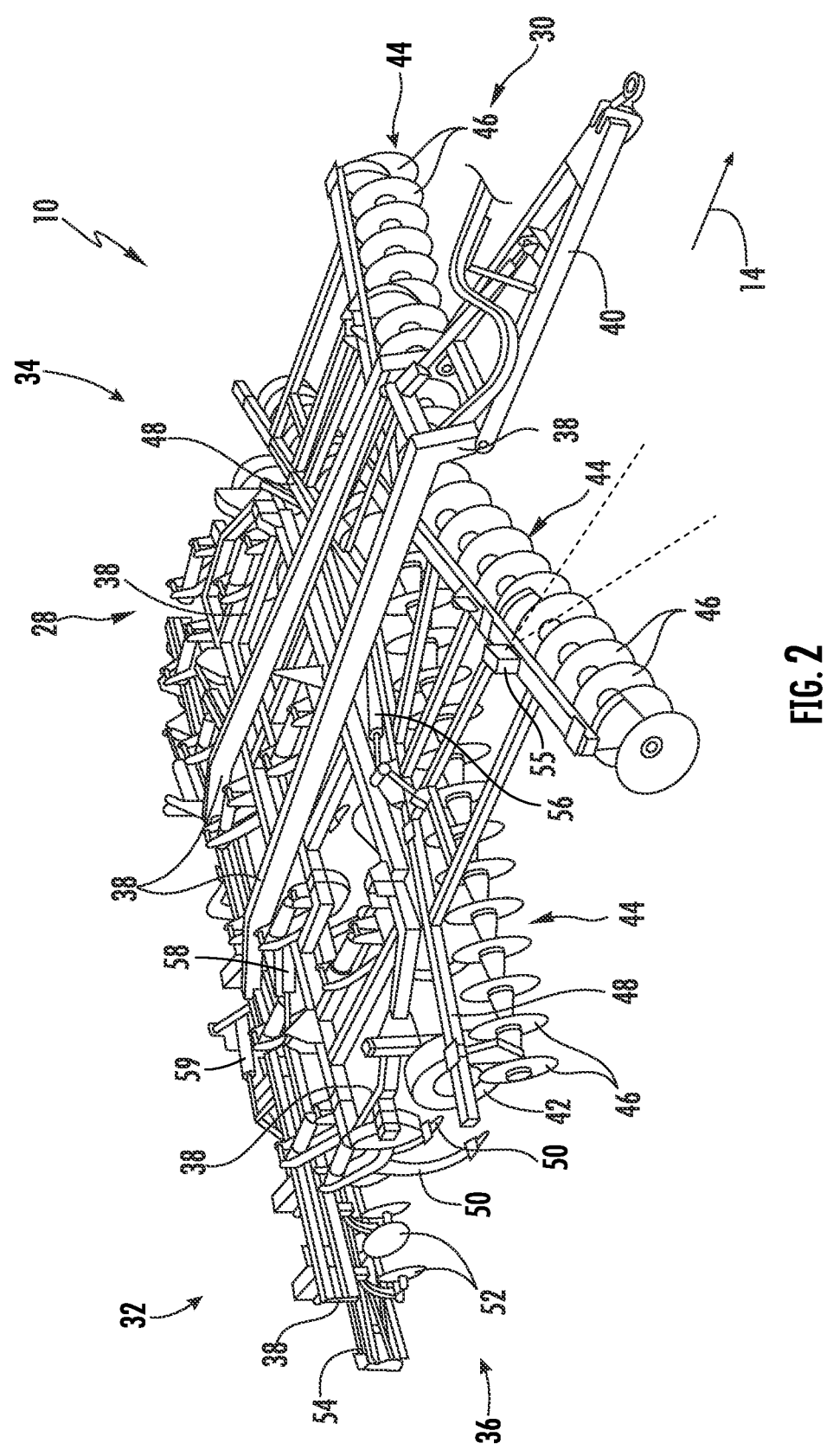
FIG. 2 illustrates another perspective view of the agricultural implement shown in FIG. 1 in accordance with aspects of the present subject matter.

Referring now to the drawings, FIGS. 1 and 2 illustrate differing perspective views of one embodiment of an agricultural implement 10 in accordance with aspects of the present subject matter. Specifically, FIG. 1 illustrates a perspective view of the agricultural implement 10 coupled to a work vehicle 12. Additionally, FIG. 2 illustrates a perspective view of the implement 10, particularly illustrating various components of the implement 10.

In general, the implement 10 may be configured to be towed across a field in a direction of travel (e.g., as indicated by arrow 14 in FIG. 1) by the work vehicle 12. As shown, the implement 10 may be configured as a tillage implement, and the work vehicle 12 may be configured as an agricultural tractor. However, in other embodiments, the implement 10 may be configured as any other suitable type of implement, such as a seed-planting implement, a fertilizer-dispensing implement, and/or the like. Similarly, the work vehicle 12 may be configured as any other suitable type of vehicle, such as an agricultural harvester, a self-propelled sprayer, and/or the like.

As shown in FIG. 1, the work vehicle 12 may include a pair of front track assemblies 16, a pair or rear track assemblies 18, and a frame or chassis 20 coupled to and supported by the track assemblies 16, 18. An operator's cab 22 may be supported by a portion of the chassis 20 and may house various input devices for permitting an operator to control the operation of one or more components of the work vehicle 12 and/or one or more components of the implement 10. Additionally, as is generally understood, the work vehicle 12 may include an engine 24 and a transmission 26 mounted on the chassis 20. The transmission 26 may be operably coupled to the engine 24 and may provide variably adjusted gear ratios for transferring engine power to the track assemblies 16, 18 via a drive axle assembly (not shown) (or via axles if multiple drive axles are employed).

As shown in FIGS. 1 and 2, the implement 10 may include a frame 28. More specifically, as shown in FIG. 2, the frame 28 may extend longitudinally between a forward end 30 and an aft end 32. The frame 28 may also extend laterally between a first side 34 and a second side 36. In this respect, the frame 28 generally includes a plurality of structural frame members 38, such as beams, bars, and/or the like, configured to support or couple to a plurality of components. Furthermore, a hitch assembly 40 may be connected to the frame 28 and configured to couple the implement 10 to the work vehicle 12. Additionally, a plurality of wheels 42 (one is shown) may be coupled to the frame 28 to facilitate towing the implement 10 in the direction of travel 14.

In several embodiments, the frame 28 may be configured to support various ground-engaging tools. For instance, the frame 28 may support one or more gangs or sets 44 of disk blades 46. Each disk blade 46 may be configured to penetrate into or otherwise engage the soil as the implement 10 is being pulled through the field. In this regard, the various disk gangs 44 may be oriented at an angle relative to the direction of travel 14 to promote more effective tilling of the soil. In the embodiment shown in FIGS. 1 and 2, the implement 10 includes four disk gangs 44 supported on the frame 28 adjacent to its forward end 30. However, it should be appreciated that, in alternative embodiments, the implement 10 may include any other suitable number of disk gangs 44, such as more or fewer than four disk gangs 44. Furthermore, in one embodiment, the disk gangs 44 may be mounted to the frame 28 at any other suitable location, such as adjacent to its aft end 32.

Moreover, as shown, in one embodiment, the implement frame 28 may be configured to support other ground-engaging tools. For instance, in the illustrated embodiment, the frame 28 is configured to support a plurality of shanks 50 configured to rip or otherwise till the soil as the implement 10 is towed across the field. Furthermore, in the illustrated embodiment, the frame 28 is also configured to support one or more finishing tools, such as a plurality of leveling blades 52 and/or rolling (or crumbler) basket assemblies 54 rotatable relative to the frame 28. However, in other embodiments, any other suitable ground-engaging tools may be coupled to and supported by the implement frame 28, such as a plurality closing disks.

Additionally, in several embodiments, the implement 10 may include a plurality of actuators configured to adjust the positions of the implement 10 and/or various ground-engaging tools coupled thereto. For example, in some embodiments, the implement 10 may include a plurality of disk gang actuators 56 (one is shown in FIG. 2), with each disk gang actuator 56 being configured to move or otherwise adjust the orientation or position of one or more of the disk gang assemblies 44 relative to the implement frame 28. Similarly, in some embodiments, the implement 10 may include a plurality of shank frame actuator(s) 58, with each shank frame actuator 58 being configured to move or otherwise adjust the orientation or position of one or more of the shanks 50 relative to the implement frame 28. Additionally, or alternatively, in some embodiments, the implement 10 may include a plurality of basket frame actuator(s) 59, with each actuator 59 being configured to move or otherwise adjust the orientation or position of a basket frame supporting one or more of the basket assemblies 54 and/or one or more of the leveling blades 52 relative to the implement frame 28.

The implement 10 and/or the work vehicle 12 may additionally be equipped with different types of field condition sensors for monitoring field conditions (e.g., soil moisture) within the field during the performance of an agricultural operation with the implement 10. For instance, one or more field condition sensor(s) 55 may be supported on the vehicle 12 and/or on the implement 10, with each of the sensor(s) 55 being configured to generate data indicative of one or more field conditions, particularly data indicative of a moisture content of the field.

In some instances, the sensor(s) 55 may be non-contact sensors spaced apart from and above a surface of the field during an agricultural operation with the implement 10 while having a field of view generally directed towards a portion of the field. In some embodiments, the field of view of each of the non-contact sensor(s) 55 is directed towards a portion of the field that has yet to be worked by the implement 10, such that there is sufficient time to process the data generated by the non-contact sensor(s) 55 before the implement 10 passes over the detected area. For instance, the field of view of the sensor(s) 55 may be directed in front of the vehicle 12, in front of the implement 10 (e.g., at least in front of the ground-engaging tool(s) being monitored for plugging), and/or towards an adjacent swath to the current swath the implement is currently traveling in that the implement 10 will traverse during a later pass. However, it should be appreciated that, in some embodiments, the non-contact sensor(s) 55 may be mounted on a vehicle configured to perform a separate pass across the field, such as on an unmanned aerial vehicle (UAV) and/or the like, such that the sensor(s) 55 may generate data before and/or during the performance of the agricultural operation with the agricultural implement 10. The non-contact field condition sensor(s) 55 may be any suitable non-contact sensor, such as a ground penetrating radar (GPR) sensor(s), such as a single-frequency GPR sensor or a multi-frequency GPR sensor, a reflectance sensor (e.g., a near-infrared sensor), a camera (e.g., a multispectral camera, an infrared camera, and/or the like), a gamma ray sensor, and/or the like.

In some embodiments, one or more of the sensor(s) 55 is configured as a contact-based sensor, configured to engage the field as the implement 10 performs an operation within the field. In some instances, the contact-based sensor(s) 55 are configured to contact a portion of the field yet to be worked by the implement 10, such that there is sufficient time to process the data generated by the contact-based sensor(s) 55 before the implement 10 passes over the detected area. For instance, the contact-based sensor(s) 55 may be configured to engage the field in front of the vehicle 12, in front of the implement 10 (e.g., at least in front of the ground-engaging tool(s) being monitored for plugging), and/or towards an adjacent swath to the current swath the implement is currently traveling in that the implement 10 will traverse during a later pass. However, it should be appreciated that, in some embodiments, the contact-based sensor(s) 55 may be mounted on a separate vehicle configured to perform a separate pass across the field, such that the contact-based sensor(s) 55 may generate data before and/or during the performance of the agricultural operation with the agricultural implement 10. The contact-based field condition sensor(s) 55 may be any suitable contact-based sensor, such as a capacitance sensor.

As will be described in greater detail below, the data from the field condition sensor(s) 55 may be used to adjust the output frequency of signal transmission devices of a system for monitoring plugging of one or more of the ground-engaging tools of the implement 10 using wireless signal attenuation. For instance, targets (e.g., RFID tags) may be positioned relative to ground-engaging tool(s) being monitored for plugging such that wireless signals transmitted from a signal transmission device (e.g., RFID reader) to the targets and/or returned from the targets to the signal transmission device are at least one of attenuated or blocked when the ground-engaging tool is experiencing the plugged condition. The moisture content within the field may affect the degree of attenuation of wireless signals (e.g., radio-frequency signals). For example, the higher the moisture content within the field, the higher the degree of attenuation of wireless signals. As such, when the moisture content in the field is high, plugging may be detected when plugging has not actually occurred, or more significant plugging may be detected than is actually occurring, both of which require more frequent than necessary inspections of the ground-engaging tools and thus, reduces productivity. Thus, in accordance with aspects of the present subject matter, an output frequency at which the signal transmission device is configured to transmit the wireless signals may be adjusted based at least in part on the field conditions (e.g., moisture content) within the field before determining whether the ground-engaging tool is experiencing a plugged condition. Therefore, the adjusted output frequency may be selected to avoid false positives or over estimation of plugging severity when monitoring for a plugging condition of ground-engaging tools, which reduces inspection time and increases productivity.

Figure 3:
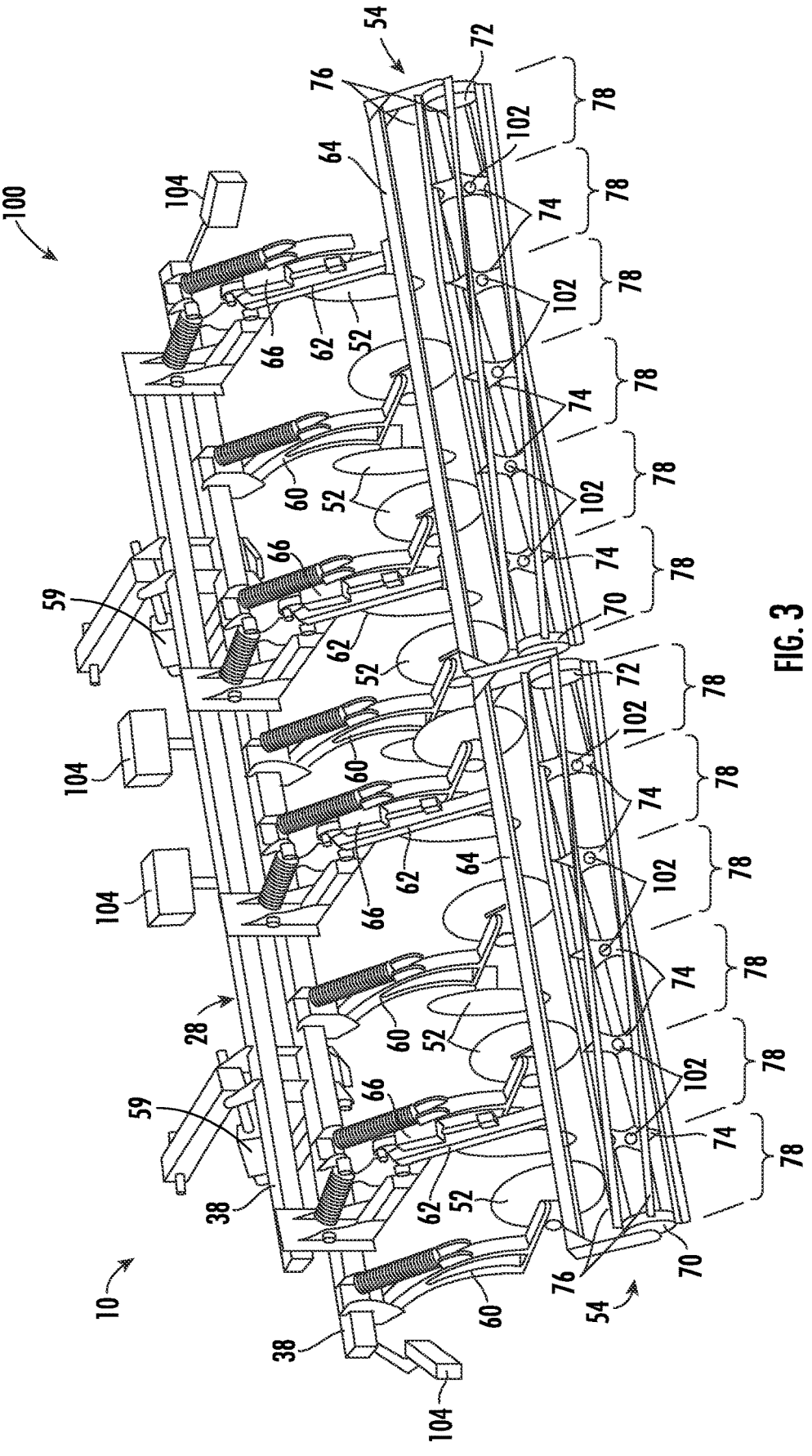
FIG. 3 illustrates a partial perspective view of finishing tools positioned at an aft end of the implement shown in FIGS. 1 and 2 in accordance with aspects of the present subject matter.

Referring now to FIG. 3, a partial, perspective view of the aft end of the implement 10 shown in FIGS. 1 and 2 is illustrated in accordance with aspects of the present subject matter, particularly illustrating a portion of the finishing tools 52, 54 of the implement 10. As shown, the various finishing tools 52, 54 may be coupled to or supported by the implement frame 28, such as by coupling each tool to a toolbar or laterally extending frame member 38 of the frame 38. For instance, as shown in FIG. 3, a blade support arm 60 may be coupled between a given frame member 38 and each leveling blade 52 or set of leveling blades 52 to support the blades 52 relative to the frame 28. Similarly, one or more basket support arms 62 may be coupled between a given frame member 38 and an associated mounting yoke or basket hanger 64 for supporting each basket assembly 54 relative to the frame 28. Additionally, as shown in FIG. 3, in one embodiment, a basket actuator 66 (e.g., a hydraulic or pneumatic cylinder) may be coupled to each basket support arm 62 to allow the down force or down pressure applied to each basket assembly 54 to be adjusted. The basket actuator(s) 66 may also allow the basket assemblies 54 to be raised off the ground, such as when the implement 10 is making a headland turn and/or when the implement 10 is being operated within its transport mode.

In several embodiments, each basket assembly 54 includes a plurality of support plates 70, 72, 74 configured to support a plurality of blades or bars 76 spaced circumferentially about the outer perimeter of the basket. For instance, as shown in FIG. 3, each basket assembly 54 includes first and second end plates 70, 72 positioned at the opposed lateral ends of the basket assembly 54 and a plurality of inner support plates 74 spaced apart laterally from one another between the end plates 70, 72. Lateral basket sections 78 are generally defined between each pair of adjacent support plates 70, 72, 74, with each basket section 78 being generally characterized by a hollow or substantially hollow interior area surrounded by the lateral portions of the bars 76 extending between the respective pair of adjacent support plates 70, 72, 74. As is generally understood, the end plates 70, 72 may be rotatably coupled to the corresponding basket hanger 64 (which, in turn, is coupled to the associated bracket support arm(s) 62) via bearings to allow the basket assembly 54 to rotate relative to the hanger/arm 64, 62 as implement 10 is being moved across the field. Additionally, in the illustrated embodiment, the bars 76 of each basket assembly 54 are configured as formed bars. However, in other embodiments, the bars 76 may have any other suitable configuration, such as flat bars, round bars, and/or the like.

Moreover, in accordance with aspects of the present subject matter, FIG. 3 also illustrates components of one embodiment of a system 100 for monitoring plugging of an agricultural implement. Specifically, in the illustrated embodiment, the system 100 is shown as being configured for use in monitoring for plugged condition(s) of the basket assemblies 54. However, in other embodiments, the system 100 may be utilized to identify a plugged condition of any other suitable ground-engaging tool(s), such as blades, disks, shanks, and/or the like.

As shown in FIG. 3, the system 100 includes one or more targets 102 and one or more signal transmission devices 104. The target(s) 102 are configured to receive wirelessly transmitted signals from the signal transmission device(s) 104 (also referred to herein simply as "signal transmitters") and to return modified wireless signals to the signal transmitter(s) 104. In general, the target(s) 102 may be configured to be positioned on or within the basket assembly 54 at a suitable location that allows the targets(s) to receive wireless signals from the signal transmitter(s) and return modified wireless signals to the signal transmitter(s) during normal, non-plugged operation of the basket assembly 54. However, with accumulation of field materials on and/or within the basket assembly 54, the wireless signals transmitted from the signal transmitter(s) 104 to the target(s) 102 and the returning modified signals transmitted from the target(s) 102 to the signal transmitter(s) 104 will become degraded or attenuated (or may be completed blocked) as the signals pass through the accumulated material. By detecting the attenuation of the signals (or the lack of any signals due to signal blockage), an associated computing system 106 (FIG. 4) of the disclosed system 100 may infer or determine that the basket assembly 54 is currently plugged or experiencing a plugged condition. Once it is determined that the basket assembly 54 is experiencing a plugged condition, an appropriate control action may then be executed, such as by notifying the operator of the plugged condition or by performing an automated adjustment of an operation of the implement 10 and/or the associated work vehicle 12.

In several embodiments, one or more of the targets 102 may be configured to be installed on or within each basket assembly 54, such as by coupling a target(s) 102 to one or more of the support plates 70, 72, 74 of the basket assembly 54. For instance, in one embodiment, a target(s) 102 may be coupled to each inner support plate 74 and/or each end plate 70, 72 such that at least one target 102 is positioned within each lateral basket section 78 of the associated basket assembly 54. By including at least one target 102 within each lateral basket section 78 of the basket assembly 54, material accumulation may be detected on a section-specific basis, thereby allowing the plugging status of each basket section 78 to be monitored individually. It should be appreciated that, in some embodiments, the target(s) 102 may additionally, or alternatively, be coupled to or supported by any other suitable component(s) of the basket assembly 54 that allows the target(s) 102 to function as described herein, such as one or more of the bars 76, an internal support shaft extending through and/or between the support plates 70, 72, 74 (if applicable), and/or any other suitable basket component.

In some embodiments, a pair of targets 102 may be associated with a given basket section 78 to provide redundancy and also allow for the collected data to be verified to increase the confidence level in identifying a plugged condition for the basket assembly 54. For example, a pair of targets 102 may be coupled to each inner support plate 74, with one target 102 being secured to one side or face of each support plate 74 and another target 102 being secured to the opposed side or face of the support plate 74. As such, if the wireless signals transmitted from a first target 102 within a basket section 78 appear to be attenuated or completely blocked as detected by the associated signal transmission device 104 (thereby indicating the associated basket section 78 is becoming plugged or is already plugged), the signals received from a second target 102 at a different location within the same basket section 78 may be referenced to confirm the existence of material accumulation within the associated basket section 78. If the signals transmitted from such second target 102 are similarly attenuated or blocked, it may be inferred with a high degree of confidence that material accumulation is occurring within the associated basket section 78. However, if the signals transmitted from the second target 102 do not appear to be attenuated or blocked, it may be necessary or desirable to analyze the wireless signals received from both targets 102 over an additional period of time before determining whether it is likely that material accumulation is occurring within the associated basket section 78.

As indicated above, each target 102 may be configured to receive a wireless (energy) signal(s) from a wireless signal transmitter 104. For instance, in one embodiment, each target 102 may be configured as an RFID tag, such as a passive RFID tag configured to receive a wireless signal and return a corresponding reply signal (e.g., modified version of the received wireless signal, such as with information identifying the RFID tag). In such an embodiment, the RFID tag may include an antenna for receiving and transmitting signals, and an integrated circuit which stores and process information to modulate and demodulate radio-frequency (RF) signals. The wireless signal transmitter(s) 104 may be an RFID interrogator or reader having a transceiver (e.g., including a transmitter and a receiver) and an associated antenna. For instance, if the targets 102 correspond to passive RFID tags, the signal transmitter(s) 104 may form part of or may be communicatively coupled to an RFID reader configured to actively transmit interrogation signals to each associated RFID tag and receive the corresponding reply signals from the tag(s) 102. It should be appreciated that, in embodiments with active RFID tags positioned on the basket assembly(ies) 54, the active RFID tags may act as wireless signal transmitters configured to transmit wireless signals without necessarily receiving an initial wireless signal from the reader(s), where the targets may then be the RFID readers positioned remotely from the tags and configured to receive the wireless signals transmitted by the active RFID tags.

In other embodiments, the target(s) and wireless signal transmitter(s) may be configured as any other suitable combination of component(s) and/or device(s) using any suitable wireless communication protocol(s) or other suitable wireless signal transmission technology. For instance, in some embodiments, the target(s) 102 and wireless signal transmitter(s) 104 may be configured to communicate using short-range wireless signals using Bluetooth, Near-Field Communications, WiFi, Zigbee, RuBee, and/or any other suitable short-range wireless communication protocol, in the form of radio waves, magnetic waves, other forms of electromagnetic waves, and/or the like.

Moreover, in several embodiments, the wireless signal transmitter(s) 104 may be configured to be installed at any suitable location relative to the target(s) 102 that allows the signal transmitter(s) 104 to transmit wireless signals to the target(s) 102 and receive the modified, reply wireless signals transmitted from the targets(s) 102 during normal, unplugged operation of the associated ground-engaging tool (e.g., basket assembly 54). For instance, when each target 102 has a given wireless transmission range, the wireless signal transmitter(s) 104 may be installed at any suitable location on the implement 10 that falls within such wireless transmission range. As shown in the illustrated embodiment, each wireless signal transmitter 104 is mounted to a portion of the implement frame 28 extending along the aft end of the implement 10, such as on the toolbar(s) or frame member(s) 38 to which the leveling discs 52 and/or basket assemblies 54 are coupled. However, in other embodiments, the wireless signal transmitter(s) 104 may be mounted to any other suitable component of the implement 10 within the wireless transmission range of the signal target(s) 102, such as on the basket support arm 62 and/or hanger 64 for one or more of the basket assemblies 54 and/or at any other suitable location.

In the illustrated embodiment, the system 100 is shown as including four wireless signal transmitters 104 spaced apart laterally along the aft end of the implement frame 28. However, in other embodiments, the system may include any other suitable number of wireless signal transmitters 104, such as three or less wireless signal transmitters 104 (including a single wireless signal transmitter) or five or more wireless signal transmitters. In general, the exact number of wireless signal transmitters 104 used within the system 100, as well as the positioning and/or orientation of the wireless signal transmitters 104, will generally vary depending on the number, configuration, and/or positioning of the associated target(s) 102. For instance, if a single target 102 or a limited number of targets 102 is/are being used within the system 100, a single wireless signal transmitter 104 may be sufficient to detect the return wireless signals transmitted from the target(s) 102. However, if multiple targets 102 are installed at various different positions and/or orientations within each basket assembly 54, it may be desirable for the system 100 to include two or more wireless signal transmitters 104 to ensure that the wireless signals transmitted from each target 102 are capable of being received by at least one of the wireless signal transmitters 104.

Figure 4:
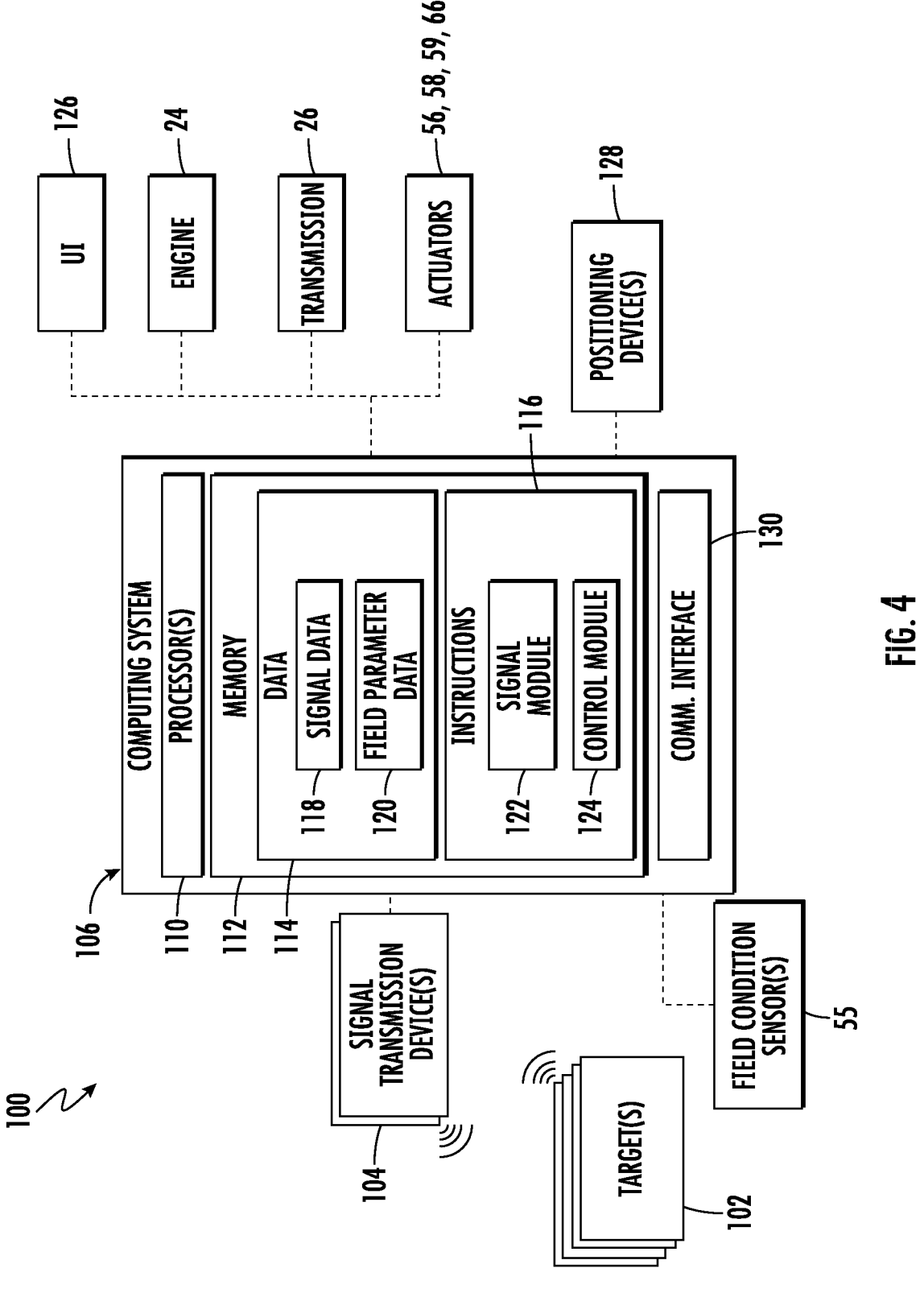
FIG. 4 illustrates a schematic view of one embodiment of a system for monitoring plugging of ground-engaging tools of an agricultural implement in accordance with aspects of the present subject matter.

Referring now to FIG. 4, a schematic view of one embodiment of a system 100 for monitoring plugging of ground-engaging tools of an agricultural implement is illustrated in accordance with aspects of the present subject matter. In general, the system 100 will be described with reference to the implement shown in FIGS. 1 and 2 and the basket assembly 54 and associated system components shown in FIG. 3. However, in other embodiments, the disclosed system 100 may be utilized to monitor ground-engaging tool plugging in association with any other suitable agricultural implement having any other suitable implement configuration and/or with any other suitable ground-engaging tool(s) having any other suitable tool configuration. Additionally, it should be appreciated that, for purposes of illustration, communicative links or electrical couplings of the system 100 shown in FIG. 4 are indicated by dashed lines.

As indicated above, in several embodiments, the system 100 may include a computing system 106 and various other components configured to be communicatively coupled to and/or controlled by the computing system 106, such as the target(s) 102, the signal transmission device(s) 104, field condition sensors (e.g., the field condition sensor(s) 55), drive components of the work vehicle 12 (e.g., the engine 24, the transmission 26, and/or the like), one or more actuator(s) of the implement 10 (e.g., the disk gang actuator(s) 56, the shank frame actuator(s) 58, the basket frame actuator(s) 59, the basket actuator(s) 66, and/or the like), and/or any other suitable components. Moreover, in some instances, the system 100 may include a user interface (e.g., user interface(s) 126). The user interface(s) 126 may include, without limitation, any combination of input and/or output devices that allow an operator to provide operator inputs to the computing system 106 and/or that allow the computing system 106 to provide feedback to the operator, such as a key board, keypad, pointing device, buttons, knobs, touch sensitive screen, mobile device, audio input device, audio output device, and/or the like. Additionally, in some instances, the system 100 may include one or more positioning devices communicatively coupled to the computing system 106 and configured to generate data indicative of the location of the agricultural implement 10 and/or vehicle 12, such as a satellite navigation positioning device (e.g., a GPS system, a Galileo positioning system, a Global Navigation satellite system (GLONASS), a BeiDou Satellite Navigation and Positioning system, a dead reckoning device, and/or the like).

In general, the computing system 106 may correspond to any suitable processor-based device(s), such as a computing device or any combination of computing devices. Thus, as shown in FIG. 4, the computing system 106 may generally include one or more processor(s) 110 and associated memory devices 112 configured to perform a variety of computer-implemented functions (e.g., performing the methods, steps, algorithms, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory 112 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory 112 may generally be configured to store information accessible to the processor(s) 110, including data 114 that can be retrieved, manipulated, created and/or stored by the processor(s) 110 and instructions 116 that can be executed by the processor(s) 110.

It should be appreciated that the computing system 106 may correspond to an existing controller for the implement 10 and/or the vehicle 12 or may correspond to a separate processing device. For instance, in one embodiment, the computing system 106 may form all or part of a separate plug-in module that may be installed in operative association with the implement 10 and/or the vehicle 12 to allow for the disclosed system and method to be implemented without requiring additional software to be uploaded onto existing control devices of the implement 10 and/or the vehicle 12.

In several embodiments, the data 114 may be stored in one or more databases. For example, the memory 112 may include a signal database 118 for storing the signals received by the signal transmission device(s) 104 from each signal target 102 and/or data associated with the received signals. Specifically, in one embodiment, data associated with the signal strength of the signals received by the signal transmission device(s) 104 may be stored within the signal database 118. For instance, signal strength data may be stored as a Received Signal Strength Indicator (RSSI) value for the wireless signals received from each target 102. As will be described below, the RSSI value associated with the wireless signals received from a given target 102 may be compared to one or more associated predetermined signal strength thresholds (RSSI values) to facilitate the determination of whether the signals are attenuated due to material accumulation between such target 102 and the associated signal transmission device(s) 104. The data stored in the signal database 118 may be cross-referenced with position data from the positioning device(s) 128 such that locations in the field associated with plugging may be accounted for in subsequent passes of the agricultural implement 10 and/or in subsequent agricultural operations (e.g., planting) within the field.

Additionally, as shown in FIG. 4, the memory 112 may include a field parameter database 120 for storing information related to one or more parameters of the field being processed during the performance of the associated agricultural operation (e.g., a tillage operation). For instance, in one embodiment, moisture data associated with the moisture content or level of the soil within the field may be stored within the field parameter database 120. As indicated above, the wetness or moisture content of the soil may impact the magnitude of the signal degradation or attenuation of the wireless signals being transmitted through adjacent material accumulation. For instance, material accumulation including significantly wet soil may attenuate the signals transmitted to/from an adjacent target 102 to a greater degree than material accumulation including drier or less wet soil. Accordingly, by knowing the soil moisture within the field, the computing system 106 may be configured to more accurately assess the signals received by the signal transmission device(s) 104 from each target 102.

It should be appreciated that the moisture data may be correspond to pre-existing or predetermined moisture data stored within the field parameter database 120 or the moisture data may correspond to sensor data that is being actively collected or generated during the performance of the associated agricultural operation. For instance, in one embodiment, the computing system 106 may be provided with soil moisture data (e.g., in the form of a soil moisture map) that was collected during a previous agricultural operation or that was generated based on previously known data associated with the field conditions. Alternatively, or additionally, the moisture data may be the data generated by the field condition sensor(s) 55 supported on the implement 10 and/or vehicle 12, and/or from any other suitable moisture sensor(s). The data from the field condition sensor(s) 55 may be cross-referenced with position data from the positioning device(s) 128 such that the moisture content at different locations in the field may be mapped. In some instances, the data from the field condition sensor(s) 55 is cross-referenced to the soil type at the location in the field to more accurately determine the moisture content at the location in the field from the moisture data generated by the sensor(s) 55.

Referring still to FIG. 4, in several embodiments, the instructions 116 stored within the memory 112 of the computing system 106 may be executed by the processor(s) 110 to implement a signal module 122. In general, the signal module 122 may be configured to select an output frequency at which wireless signals are to be transmitted from the signal transmission device(s) 104 to the target(s) 102 based at least in part on the moisture content of the field and analyze the return signals received by the signal transmission device(s) 104 from each target 102 and/or the related signal data (or a lack thereof) to estimate or infer when the associated ground-engaging tool is experiencing a plugged condition.

In several embodiments, the signal module 122 may determine the moisture content within the field based at least in part on moisture data (e.g., from the field parameter database 120), then determine an adjusted or corresponding output frequency at which the signal transmission device(s) 104 transmits wireless signals to the target(s) 102 based at least in part on the moisture content within the field. Generally, the higher the moisture content of the field, the higher the output frequency is selected to be to account for the increased attenuation of the high moisture content. The signal module 122 may determine the adjusted output frequency using a look-up table, an algorithm, and/or the like stored, for example, in the memory 112, that correlates the moisture content within the field to an output frequency or range of output frequencies for the transmission of the wireless signals. In some instances, the corresponding output frequency or range of output frequencies for the moisture content is selected such that the wireless signals transmitted by the signal transmitter(s) 104 will not fully attenuate, or will only fully attenuate, between the signal transmission device(s) 104 and the target(s) 102 when the associated ground-engaging tools experience severe plugging conditions. The signal module 122 may, in some embodiments, compare the current output frequency of the signal transmission device(s) 104 to the adjusted output frequency, then adjust the output frequency from the current output frequency to the adjusted output frequency when the current output frequency differs from the adjusted output frequency. In some instances, the signal module 122 may only adjust the output frequency from the current output frequency to the adjusted output frequency when the current output frequency differs from the adjusted output frequency by at least a threshold amount.

The signal module 122 may also be configured to compare the signal strength of the wireless signals (e.g., return wireless signals) received from each target 102 at the signal transmission device(s) 104 to one or more associated signal strength thresholds. For instance, in one embodiment, various predetermined RSSI values may be stored within the memory 112 for each target 102, such as a first or non-plugged RSSI value corresponding to the expected RSSI value for the signals received from the target 102 when the associated ground-engaging tool is not plugged, a second or partially plugged RSSI value corresponding to the expected RSSI value for the signals received from the target 102 when the associated ground-engaging tool is partially plugged, and a third or fully plugged RSSI value corresponding to the expected RSSI value for the signals received from the target 102 when the associated ground-engaging tool is fully plugged. The computing system 106 may be configured to continuously monitor the current RSSI value for the signals received from each target 102 relative to the relevant predetermined RSSI value(s) defined for such target 102 to assess the plugging status of the ground-engaging tool (or at least the plugging status of the tool in the area of the associated target 102). By doing so, the computing system 106 may be configured to identify when the current RSSI value for a given target 102 begins to decrease from the expected "non-plugged" RSSI value as the tool becomes plugged in the area adjacent to such target 102. Once the current RSSI value drops below an associated plugging-related signal strength threshold (e.g., the partially plugged RSSI value described above) or outside a signal strength threshold range, the computing system 106 may then infer or estimate that the ground-engaging tool is currently experiencing a plugged condition and may initiate appropriate control actions in response to the detection of the plugged condition.

Additionally, the computing system 106 may be configured to identify the severity of any detected plugged condition based on a magnitude of the signal strength of the associated wireless signals. In this regard, by providing multiple plugging-related signal strength thresholds (e.g., the partially and fully plugged RSSI values described above), the computing system 106 may infer or estimate the severity of the plugged condition by comparing the current RSSI value to each of such thresholds, which may impact the selection of the appropriate control action(s) to be executed (e.g., notifying the operator when it is detected that the tool is partially plugged versus performing an automated control action to adjust the operation of the implement when it is detected that the tool is fully plugged).

As indicated above, the magnitude of the attenuation or degradation of the signals deriving from each target 102 may vary depending on the moisture content of the soil through which the signals are being transmitted. Thus, in several embodiments, a moisture correction factor may be applied to the plugging-related signal strength threshold(s) used to assess the current RSSI value associated with the signals received from each target 102. For instance, a look-up table may be stored within the memory 112 that correlates soil moisture values to corresponding moisture correction factors associated with the degree to which each moisture level degrade or attenuates the wireless signals. In such instance, by knowing the soil moisture within the field (e.g., via the soil moisture data stored within the field parameter database 120), an appropriate correction factor may be selected for modifying the signal strength threshold(s) to account for variations in the soil moisture. The modified signal strength threshold(s) may then be used to analyze the current RSSI value(s) for each target 102 when assessing the plugging status of the associated ground-engaging tool. Alternatively, or additionally, in some embodiments, the predetermined RSSI values may be selected based at least in part on the moisture content within the field to correspond to the adjusted output frequency.

The signal module 122 may be configured to determine the source of each wireless signal received by the wireless signal transmitter(s) 104, such as by identifying a unique code or number (e.g., a serial number) transmitted from each target 102. By doing so, the signal module 122 may be configured to not only assess the signal strength of the return signals received from each target 102, but also determine when signals are not being received from a given target(s) 102. Based on such a determination, the computing system 106 may infer or estimate that the ground-engaging tool is plugged at or adjacent to the area of the target(s) 102 from which signals are not currently being received.

Referring still to FIG. 4, the instructions 116 stored within the memory 112 of the computing system 106 may also be executed by the processor(s) 110 to implement a control module 124. In general, the control module 124 may be configured to initiate a control action when it is determined that a ground-engaging tool of the implement 10 is experiencing a plugged condition. As indicated above, in one embodiment, the control module 124 may be configured to provide a notification to the operator of the vehicle 12 and/or implement 10 indicating that material accumulation is present on, within, and/or adjacent to one or more of the ground-engaging tools of the implement 10. For instance, in one embodiment, the control module 124 may control an operation of the user interface 126 to indicate (e.g., cause a visual or audible notification or indicator to be presented) to an operator that the ground-engaging tool(s) are plugged, recommend an action to mitigate the plugging, and/or the like.

In other embodiments, the control module 124 may be configured to execute an automated control action designed to adjust the operation of the implement 10 and/or the vehicle 12. For instance, in one embodiment, the computing system 106 may be configured to increase or decrease the operational or ground speed of the implement 10 in an attempt to reduce the amount of material accumulation and/or to limit further material accumulation. For instance, as shown in FIG. 4, the computing system 106 may be communicatively coupled to both the engine 24 and the transmission 26 of the work vehicle 12. In such an embodiment, the computing system 106 may be configured to adjust the operation of the engine 24 and/or the transmission 26 in a manner that increases or decreases the ground speed of the work vehicle 12 and, thus, the ground speed of the implement 10, such as by transmitting suitable control signals for controlling an engine or speed governor (not shown) associated with the engine 24 and/or transmitting suitable control signals for controlling the engagement/disengagement of one or more clutches (not shown) provided in operative association with the transmission 26. It should be appreciated that computing system 106 may also be configured to decrease the ground speed in a manner that brings the implement 10 and the vehicle 12 to a complete stop.

In addition to the adjusting the ground speed of the implement 10 and the vehicle 12 (or as an alternative thereto), the computing system 106 may also be configured to adjust an operating parameter associated with the ground-engaging tools of the implement 10. For instance, as shown in FIG. 4, the computing system 106 may be configured to control the operation of one or more actuators 56, 58, 59, 66 (e.g., control valves, pumps, and/or the like associated with the actuators 56, 58, 59, 66) of the implement 10 to automatically adjust the penetration depth, the down force, and/or any other suitable operating parameter associated with the ground-engaging tools of the implement 10 to mitigate plugging. For instance, by controlling the operation of the basket actuators 66, the computing system 106 may automatically adjust the down force or down pressure applied to the associated basket assembly 54 (e.g., cyclically increase and decrease engagement with the field), which may help mitigate plugging. Additionally, or alternatively, the computing system 106 may control the operation of the basket actuator 66 to raise and lower the associated basket assembly 54 relative to the ground to indicate to an operator that the basket assembly 54 needs to be de-plugged.

Moreover, as shown in FIG. 4, the computing system 106 may also include a communications interface 130 to provide a means for the computing system 106 to communicate with any of the various other system components described herein. For instance, one or more communicative links or interfaces (e.g., one or more data buses) may be provided between the communications interface 130 and the signal transmission device(s) 104 to allow the computing system 106 to control the signal transmission device(s) output frequency for transmitting the output signals and/or to receive the return signals (and/or related signal data) received by the signal transmission device(s) 104 from the target(s) 102. Similarly, one or more communicative links or interfaces (e.g., one or more data buses) may be provided between the communications interface 130 and the engine 24, the transmission 26, the user interface 126, the actuator(s) 56, 58, 59, 66, and/or the like to allow the computing system 106 to control the operation of and/or otherwise communicate with such system components. Moreover, one or more communicative links or interfaces (e.g., one or more data buses) may be provided between the communications interface 130 and the field condition sensor(s) 55 to allow the computing system 106 to control the field condition sensor(s) 55 to collect field condition data and/or to receive the field condition data from the field condition sensor(s). Additionally, one or more communicative links or interfaces (e.g., one or more data buses) may be provided between the communications interface 130 and the positioning device(s) 128 to allow the computing system 106 to control the positioning device(s) 128 to collect the position data and/or to receive the position data from the positioning device(s) 128.

Referring now to FIG. 5, a flow diagram of one embodiment of a method 200 for monitoring plugging of ground-engaging tools of an agricultural implement is illustrated in accordance with aspects of the present subject matter. In general, the method 200 will be described herein with reference to the agricultural implement 10, the basket assembly 54, and the system 100 described above with reference to FIGS. 1-4. However, it should be appreciated by those of ordinary skill in the art that the disclosed method 200 may generally be implemented with any agricultural implement having any suitable implement configuration, any ground-engaging tool having any suitable tool configuration, and/or any system having any suitable system configuration. In addition, although FIG. 5 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 5, at (202), the method 200 may include receiving moisture data indicative of a moisture content within a field as a ground-engaging tool of an agricultural implement works the field. For instance, as described above, the computing system 106 may receive moisture data, the moisture data being indicative of a moisture content within the field as a ground-engaging tool (e.g., disk gangs 44, shanks 50, leveling disks 52, and/or basket assemblies 54) of the agricultural implement 10 works the field as the agricultural implement 10 is moved across the field.

Further, at (204), the method 200 may include adjusting an output frequency at which a signal transmission device is configured to transmit wireless signals from a current output frequency to an adjusted output frequency based at least in part on the moisture data. For example, as discussed above, the computing system 106 may be configured to adjust an output frequency at which the signal transmission device(s) 104 is configured to transmit wireless signals, the output frequency being adjusted from a current output frequency to an adjusted output frequency, based on the moisture data.

Moreover, at (206), the method 200 may include determining when the ground-engaging tool is experiencing a plugged condition based at least in part on an attenuation parameter of the wireless signals transmitted by the signal transmission device at the adjusted output frequency and received by a target provided in operative association with the ground-engaging tool. For instance, as discussed above, the computing system 106 may determine when the ground-engaging tool (e.g., disk gangs 44, shanks 50, leveling disks 52, and/or basket assemblies 54) is experiencing a plugged condition based at least in part on an attenuation parameter of the wireless signals transmitted by the signal transmission device 104 at the adjusted output frequency and received by the target 102 (e.g., based on the return signal received by the signal transmission device 104 from the target 102) provided in operative association with the ground-engaging tool, where the target 102 is spaced apart from the signal transmission device 104.

Additionally, at (208), the method 200 may include controlling an operation of a device associated with the agricultural implement when the ground-engaging tool is experiencing the plugged condition. For example, as described above, the computing system 106 may automatically control an operation of the user interface(s) 126, the engine 24, the transmission 26, the actuator(s) 56, 58, 59, 66, and/or the like when the ground-engaging tool (e.g., disk gangs 44, shanks 50, leveling disks 52, and/or basket assemblies 54) is experiencing the plugged condition.

It is to be understood that the steps of the method 200 are performed by the computing system 106 upon loading and executing software code or instructions which are tangibly stored on a tangible computer readable medium, such as on a magnetic medium, e.g., a computer hard drive, an optical medium, e.g., an optical disk, solid-state memory, e.g., flash memory, or other storage media known in the art. Thus, any of the functionality performed by the computing system 106 described herein, such as the method 200, is implemented in software code or instructions which are tangibly stored on a tangible computer readable medium. The computing system 106 loads the software code or instructions via a direct interface with the computer readable medium or via a wired and/or wireless network. Upon loading and executing such software code or instructions by the computing system 106, the computing system 106 may perform any of the functionality of the computing system 106 described herein, including any steps of the method 200 described herein.

The term "software code" or "code" used herein refers to any instructions or set of instructions that influence the operation of a computer or computing system. They may exist in a computer-executable form, such as machine code, which is the set of instructions and data directly executed by a computer's central processing unit or by a computing system, a human-understandable form, such as source code, which may be compiled in order to be executed by a computer's central processing unit or by a computing system, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a computing system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An agricultural system for monitoring plugging of ground-engaging tools of an agricultural implement, the agricultural system comprising:

a ground-engaging tool of an agricultural implement, the ground-engaging tool being configured to work a field as the agricultural implement is moved across the field;

a signal transmission device configured to transmit wireless signals;

a target provided in operative association with the ground-engaging tool and spaced apart from the signal transmission device, the target being configured to receive the wireless signals transmitted from the signal transmission device; and a computing system configured to:

receive moisture data indicative of a moisture content within the field;

adjust an output frequency for the signal transmission device to transmit the wireless signals from a current output frequency to an adjusted output frequency based at least in part on the moisture data; and determine when the ground-engaging tool is experiencing a plugged condition based at least in part on an attenuation parameter of the wireless signals transmitted by the signal transmission device at the adjusted output frequency and received by the target.

2. The agricultural system of claim 1, wherein the computing system is configured to adjust the output frequency from the current output frequency to the adjusted output frequency based at least in part on the moisture data by:

determining the moisture content within the field based at least in part on the moisture data;

determining the adjusted output frequency based at least in part on the moisture content within the field;

comparing the current output frequency to the adjusted output frequency; and adjusting the output frequency from the current output frequency to the adjusted output frequency when the current output frequency differs from the adjusted output frequency by at least a threshold amount.

3. The agricultural system of claim 1, wherein the computing system is configured to automatically control an operation of the signal transmission device to adjust the output frequency from the current output frequency to the adjusted output frequency.

4. The agricultural system of claim 1, wherein the attenuation parameter comprises a signal strength of the wireless signals, the computing system being configured to determine when the ground-engaging tool is experiencing the plugged condition based at least in part on the signal strength of the wireless signals received by the target from the signal transmission device.

5. The agricultural system of claim 4, wherein the computing system is configured determine when the ground-engaging tool is experiencing the plugged condition by comparing the signal strength of the wireless signals received by the target to at least one predetermined signal strength threshold associated with the adjusted output frequency and determining that the ground-engaging tool is experiencing the plugged condition when the signal strength is outside of the at least one predetermined signal strength threshold.

6. The agricultural system of claim 1, wherein the computing system is further configured to perform a control action when the ground-engaging tool is experiencing the plugged condition.

7. The agricultural system of claim 1, wherein the signal transmission device is installed relative to the ground-engaging tool such that the wireless signals transmitted from the signal transmission device to the target are at least one of attenuated or blocked when the ground-engaging tool is experiencing the plugged condition.

8. The agricultural system of claim 1, wherein the target comprises an RFID tag, the RFID tag being configured to transmit a return signal having a strength in accordance with attenuation of the wireless signals transmitted from the signal transmission device.

9. The agricultural system of claim 8, wherein the computing system is further configured to:

receive data indicative of the return signal; and determine the attenuation parameter of the wireless signals transmitted by the signal transmission device based at least in part on the return signal.

10. The agricultural system of claim 1, further comprising a moisture sensor supported on the agricultural implement, the moisture sensor being configured to generate the moisture data indicative of the moisture content within the field, wherein the computing system is configured to receive the moisture data generated by the moisture sensor.

11. The agricultural system of claim 1, wherein the ground-engaging tool is a basket assembly configured to be supported by an agricultural implement such that the basket assembly is rotatable relative to the agricultural implement, the basket assembly defining an at least partially hollow interior within which field materials can accumulate as the basket assembly moves across the field.

12. An agricultural method for monitoring plugging of ground-engaging tools of an agricultural implement, the agricultural method comprising:

receiving, with a computing system, moisture data indicative of a moisture content within a field as a ground-engaging tool of an agricultural implement works the field as the agricultural implement is moved across the field;

adjusting, with the computing system, an output frequency at which a signal transmission device is configured to transmit wireless signals from a current output frequency to an adjusted output frequency based at least in part on the moisture data;

determining, with the computing system, when the ground-engaging tool is experiencing a plugged condition based at least in part on an attenuation parameter of the wireless signals transmitted by the signal transmission device at the adjusted output frequency and received by a target provided in operative association with the ground-engaging tool, the target being spaced apart from the signal transmission device; and controlling, with the computing system, an operation of a device associated with the agricultural implement when the ground-engaging tool is experiencing the plugged condition.

13. The agricultural method of claim 12, wherein adjusting the output frequency from the current output frequency to the adjusted output frequency based at least in part on the moisture data comprises:

determining, with the computing system, the moisture content within the field based at least in part on the moisture data;

determining, with the computing system, the adjusted output frequency based at least in part on the moisture content within the field;

comparing, with the computing system, the current output frequency to the adjusted output frequency; and adjusting, with the computing system, the output frequency from the current output frequency to the adjusted output frequency when the current output frequency differs from the adjusted output frequency by at least a threshold amount.

14. The agricultural method of claim 12, wherein the attenuation parameter comprises a signal strength of the wireless signals, wherein determining when the ground-engaging tool is experiencing the plugged condition comprises determining when the ground-engaging tool is experiencing the plugged condition based at least in part on the signal strength of the wireless signals received by the target from the signal transmission device.

15. The agricultural method of claim 14, wherein determining when the ground-engaging tool is experiencing the plugged condition comprises comparing the signal strength of the wireless signals received by the target to at least one predetermined signal strength threshold associated with the adjusted output frequency and determining when the ground-engaging tool is experiencing the plugged condition when the signal strength is outside of the at least one predetermined signal strength threshold.

16. The agricultural method of claim 12, wherein the signal transmission device is installed relative to the ground-engaging tool such that the wireless signals transmitted from the signal transmission device to the target are at least one of attenuated or blocked when the ground-engaging tool is experiencing the plugged condition.

17. The agricultural method of claim 12, wherein the target comprises an RFID tag, the RFID tag being configured to transmit a return signal having a strength in accordance with attenuation of the wireless signals transmitted from the signal transmission device.

18. The agricultural method of claim 17, further comprising:

receiving, with the computing system, data indicative of the return signal; and determining, with the computing system, the attenuation parameter of the wireless signals transmitted by the signal transmission device based at least in part on the return signal.

19. The agricultural method of claim 12, wherein receiving the moisture data comprises receiving the moisture data generated by a moisture sensor supported on the agricultural implement.

20. The agricultural method of claim 12, wherein the ground-engaging tool is a basket assembly configured to be supported by an agricultural implement such that the basket assembly is rotatable relative to the agricultural implement, the basket assembly defining an at least partially hollow interior within which field materials can accumulate as the basket assembly moves across the field.

* * * * *